US011033617B2

(12) United States Patent
Cheng et al.

(10) Patent No.: US 11,033,617 B2
(45) Date of Patent: Jun. 15, 2021

(54) DUCK HEPATITIS A VIRUS TYPE 3 MUTANT CH-P60-117C AND CONSTRUCTION THEREOF

(71) Applicant: SICHUAN AGRICULTURAL UNIVERSITY, Sichuan (CN)

(72) Inventors: Anchun Cheng, Sichuan (CN); Xingjian Wen, Sichuan (CN); Mingshu Wang, Sichuan (CN); Liping Wu, Sichuan (CN)

(73) Assignee: SICHUAN AGRICULTURAL UNIVERSITY, Chengdu (CN)

( * ) Notice: Subject to any disclaimer, the term of this patent is extended or adjusted under 35 U.S.C. 154(b) by 0 days.

(21) Appl. No.: 16/921,899

(22) Filed: Jul. 6, 2020

(65) Prior Publication Data

US 2021/0008196 A1 Jan. 14, 2021

Related U.S. Application Data

(63) Continuation of application No. PCT/CN2019/125293, filed on Dec. 13, 2019.

(30) Foreign Application Priority Data

Jun. 24, 2019 (CN) ......................... 201910551115.2

(51) Int. Cl.

| | |
|---|---|
| ***C12N 7/00*** | (2006.01) |
| ***A61K 39/29*** | (2006.01) |
| ***A61P 31/14*** | (2006.01) |
| *A61K 39/00* | (2006.01) |

(52) U.S. Cl.

CPC .............. *A61K 39/29* (2013.01); *A61P 31/14* (2018.01); *C12N 7/00* (2013.01); *A61K 2039/525* (2013.01); *A61K 2039/552* (2013.01); *C12N 2770/32421* (2013.01); *C12N 2770/32434* (2013.01); *C12N 2770/32452* (2013.01)

(58) Field of Classification Search

None

See application file for complete search history.

(56) References Cited

FOREIGN PATENT DOCUMENTS

| | | |
|---|---|---|
| CN | 109797139 A | 5/2019 |
| CN | 110283835 A | 9/2019 |
| CN | 110295180 A | 10/2019 |

OTHER PUBLICATIONS

Xingjian Wen et al., Mutations in VP0 and 2C Proteins of Duck Hepatitis A Virus Type 3 Attenuate Viral Infection and Virulence,Sep. 11, 2019, No. 3, vol. 7.

Xumin Ou et al.,Incompatible Translation Drives a Convergent Evolution and Viral Attenuation During the Development of Live Attenuated Vaccine,Jul. 18, 2018,vol. 8.

*Primary Examiner* — Nianxiang Zou

(57) ABSTRACT

Disclosed herein are a duck hepatitis A virus type 3 (DHAV-3) mutant CH-P60-117C and a construction method thereof. The DHAV-3 mutant CH-P60-117C is constructed by mutating A at position 117 of 5'-UTR of the genome of the DHAV-3 virulent strain to C; mutating T at position 1142 to A to mutate tyrosine-164 of VP0 protein of the parent strain to asparagine; and mutating C at position 4334 to A so that leucine-71 of the viral protein 2C of the parent strain is mutated to isoleucine.

6 Claims, 2 Drawing Sheets

Specification includes a Sequence Listing.

SEQUENCE LISTING

```
<160> NUMBER OF SEQ ID NOS: 27

<210> SEQ ID NO 1
<211> LENGTH: 31
<212> TYPE: DNA
<213> ORGANISM: Artificial Sequence
<220> FEATURE:
<223> OTHER INFORMATION: synthetic

<400> SEQUENCE: 1

tagttattaa tagtaatcaa ttacggggtc a                                    31


<210> SEQ ID NO 2
<211> LENGTH: 40
<212> TYPE: DNA
<213> ORGANISM: Artificial Sequence
<220> FEATURE:
<223> OTHER INFORMATION: synthetic

<400> SEQUENCE: 2

acaccacagc cgctttcaaa cggttcacta aaccagctct                           40


<210> SEQ ID NO 3
```

-continued

<211> LENGTH: 40
<212> TYPE: DNA
<213> ORGANISM: Artificial Sequence
<220> FEATURE:
<223> OTHER INFORMATION: synthetic

<400> SEQUENCE: 3
agagctggtt tagtgaaccg tttgaaagcg gctgtggtgt 40

<210> SEQ ID NO 4
<211> LENGTH: 27
<212> TYPE: DNA
<213> ORGANISM: Artificial Sequence
<220> FEATURE:
<223> OTHER INFORMATION: synthetic

<400> SEQUENCE: 4
gcctagtcct agcgctatag gactccc 27

<210> SEQ ID NO 5
<211> LENGTH: 27
<212> TYPE: DNA
<213> ORGANISM: Artificial Sequence
<220> FEATURE:
<223> OTHER INFORMATION: synthetic

<400> SEQUENCE: 5
gggagtccta tagcgctagg actaggc 27

<210> SEQ ID NO 6
<211> LENGTH: 22
<212> TYPE: DNA
<213> ORGANISM: Artificial Sequence
<220> FEATURE:
<223> OTHER INFORMATION: synthetic

<400> SEQUENCE: 6
caacctgcca aaagtcaaac ca 22

<210> SEQ ID NO 7
<211> LENGTH: 25
<212> TYPE: DNA
<213> ORGANISM: Artificial Sequence
<220> FEATURE:
<223> OTHER INFORMATION: synthetic

<400> SEQUENCE: 7
tcactggatc taacaatgtg gatgc 25

<210> SEQ ID NO 8
<211> LENGTH: 25
<212> TYPE: DNA
<213> ORGANISM: Artificial Sequence
<220> FEATURE:
<223> OTHER INFORMATION: synthetic

<400> SEQUENCE: 8
gcatccacat tgttagatcc agtga 25

<210> SEQ ID NO 9
<211> LENGTH: 26
<212> TYPE: DNA
<213> ORGANISM: Artificial Sequence
<220> FEATURE:
<223> OTHER INFORMATION: synthetic

<400> SEQUENCE: 9
attctgttac acctttacgc cccaca 26

<210> SEQ ID NO 10
<211> LENGTH: 23
<212> TYPE: DNA
<213> ORGANISM: Artificial Sequence
<220> FEATURE:
<223> OTHER INFORMATION: synthetic

<400> SEQUENCE: 10
caacctaggt aagtgagcac gat 23

<210> SEQ ID NO 11
<211> LENGTH: 23
<212> TYPE: DNA
<213> ORGANISM: Artificial Sequence
<220> FEATURE:
<223> OTHER INFORMATION: synthetic

<400> SEQUENCE: 11
gtgctcactt acctaggttg gtt 23

<210> SEQ ID NO 12
<211> LENGTH: 22
<212> TYPE: DNA
<213> ORGANISM: Artificial Sequence
<220> FEATURE:
<223> OTHER INFORMATION: synthetic

<400> SEQUENCE: 12
tggcaacttc ctgtctaacc tg 22

<210> SEQ ID NO 13
<211> LENGTH: 25
<212> TYPE: DNA
<213> ORGANISM: Artificial Sequence
<220> FEATURE:
<223> OTHER INFORMATION: synthetic

<400> SEQUENCE: 13
acttgtgcat gatccggact gataa 25

<210> SEQ ID NO 14
<211> LENGTH: 25
<212> TYPE: DNA
<213> ORGANISM: Artificial Sequence
<220> FEATURE:
<223> OTHER INFORMATION: synthetic

<400> SEQUENCE: 14
ttatcagtcc ggatcatgca caagt 25

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
ccttgaacac tggaacccaa 20

<210> SEQ ID NO 16
<211> LENGTH: 69
<212> TYPE: DNA

-continued

<213> ORGANISM: Artificial Sequence
<220> FEATURE:
<223> OTHER INFORMATION: synthetic

<400> SEQUENCE: 16
aagtagccca ggtcggaccg cgaggaggtg gagatgccat gccgaccctt ttttttttt 60 ttagggtgg 69

<210> SEQ ID NO 17
<211> LENGTH: 59
<212> TYPE: DNA
<213> ORGANISM: Artificial Sequence
<220> FEATURE:
<223> OTHER INFORMATION: synthetic

<400> SEQUENCE: 17
cggtccgacc tgggctactt cggtaggcta agggagaaga acttgtttat tgcagctta 59

<210> SEQ ID NO 18
<211> LENGTH: 23
<212> TYPE: DNA
<213> ORGANISM: Artificial Sequence
<220> FEATURE:
<223> OTHER INFORMATION: synthetic

<400> SEQUENCE: 18
taagatacat tgatgagttt gga 23

<210> SEQ ID NO 19
<211> LENGTH: 583
<212> TYPE: DNA
<213> ORGANISM: Artificial Sequence
<220> FEATURE:
<223> OTHER INFORMATION: synthetic

<400> SEQUENCE: 19
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cgt 583

<210> SEQ ID NO 20
<211> LENGTH: 67
<212> TYPE: DNA
<213> ORGANISM: Artificial Sequence
<220> FEATURE:
<223> OTHER INFORMATION: synthetic

<400> SEQUENCE: 20
gggtcggcat ggcatctcca cctcctcgcg gtccgacctg ggctacttcg gtaggctaag 60
ggagaag 67

-continued

<210> SEQ ID NO 21
<211> LENGTH: 122
<212> TYPE: DNA
<213> ORGANISM: Artificial Sequence
<220> FEATURE:
<223> OTHER INFORMATION: synthetic

<400> SEQUENCE: 21
aacttgttta ttgcagctta taatggttac aaataaagca atagcatcac aaatttcaca 60
aataaagcat ttttttcact gcattctagt tgtggtttgt ccaaactcat caatgtatct 120
ta 122

<210> SEQ ID NO 22
<211> LENGTH: 21
<212> TYPE: DNA
<213> ORGANISM: Artificial Sequence
<220> FEATURE:
<223> OTHER INFORMATION: synthetic

<400> SEQUENCE: 22
tgctcactta cctaggttgg t 21

<210> SEQ ID NO 23
<211> LENGTH: 21
<212> TYPE: DNA
<213> ORGANISM: Artificial Sequence
<220> FEATURE:
<223> OTHER INFORMATION: synthetic

<400> SEQUENCE: 23
tcctagcgct ataggactcc c 21

<210> SEQ ID NO 24
<211> LENGTH: 21
<212> TYPE: DNA
<213> ORGANISM: Artificial Sequence
<220> FEATURE:
<223> OTHER INFORMATION: synthetic

<400> SEQUENCE: 24
ttctcactgg atctaacaat g 21

<210> SEQ ID NO 25
<211> LENGTH: 21
<212> TYPE: DNA
<213> ORGANISM: Artificial Sequence
<220> FEATURE:
<223> OTHER INFORMATION: synthetic

<400> SEQUENCE: 25
tgtgcatgat ccggactgat a 21

<210> SEQ ID NO 26
<211> LENGTH: 7788
<212> TYPE: DNA
<213> ORGANISM: Artificial Sequence
<220> FEATURE:
<223> OTHER INFORMATION: synthetic

<400> SEQUENCE: 26
tttgaaagcg gctgtggtgt agaccatttt ctggcgcttg gttcagccag tatggtctca 60
ccacagtctg cttggggtta ttcccaaacc ccttaattca acgcctagtc ctagcgctat 120
aggactccct atccacttgt tttaccttta ccctccacta tatagtctgt tttctggcta 180

-continued

```
ttgactttgg ctttggtttt tgactcatgt ctaagtctct atagattttg tagtggttag    240
cctaccaccc cttggccact aattcttggc ttcttgtttt gggatccacc atatcttgga    300
ggtggtgctg aaatattgca agccacttgg tatgtgtgta ttttccaaac atgaagctct    360
ggtgcagtgg ttttggacaa ggaaaggcta gtgtttggtc tggatatgaa ctcttgttgt    420
gaaacggatt accggtagta gcatctagtg gttccagtcc ataacatgag tgtatggtct    480
agagtggaca tagcttggat acagacacct tcagtattac tgggtgttcc agactagttc    540
ctgaggtacc aagttatgag ggatatgggg aaaacccctt tgatccacac tgcctgatag    600
ggtcgcggct ggtcgagtcc catacactat aaaaccagtt gattttcatg caatggatac    660
tctaactaaa aacattgaag atgaaactgt caagattatt ggatcctgtg ctgagaaggc    720
acaagaagca atctctggtc ttggagcagt tgagagtgtt gcttcaacta actctgtggt    780
tgctactgca aatgctacaa caacacaaac aattcctgat ccaacagatg gttccacaga    840
tgacttttat tcatgttcct atgaggttgg ggcccagggt gacaacatct cacgtttagt    900
ccatctacac actggacagt ggtccacaca gcatggtgtt actacatgcc ttagatggtt    960
ggtcactcct ggatgttttt atacagttaa tacccaacca gcatatggac aaaccaggta   1020
ttttaggttc atcagatgtg gctaccactt ccgccttctt gtgaatgcac catctggtgc   1080
tgctggtgga ctaatgatgg tgtggatgcc ttatccatat tgccgggttc tcactggatc   1140
taacaatgtg gatgcatcag tagatcgcag gtcgttgtta aatcttccct atgccatctt   1200
ggatctgcgc accaacactg aaattgactt ggttattcca tatgtaaatt ttagaaatta   1260
tgttgaaatt actgccacag atagtgttgg tggggccata tgtgtctttg tgttgggagc   1320
ttatacacat gggtcaggaa cctccaatac tgttgattat actctctttg gtgagatgct   1380
tgaaactgac ttacaatgtc ctcggccttt taatgaccag ggtaagaaga aaccacggcg   1440
gaggccaatt cataaaccaa agagccctcc tcaagaatct cgcatcatta ttcagcctgg   1500
accaggagct gcaaatctat ccaattctag tgtggttacc atggctgaga gtgtggctct   1560
agctaatgag ggtactgcag ttgactactc aacagctggg tgtgcatcgt ctgtggatga   1620
tgtagtcatg gtgcttagac gctggcagat tgtgggtgat tttcagtggg ctaacacagt   1680
gacccctggc aatagaattg ataggtttca ggtggttttc aatcgtatgc caacctttgc   1740
tctctttttt gataagttcc agtattggag ggggtccctg gaggttaaat tattgacctt   1800
tggaagccag tttaatactg gccgctatca gatgtcatgg taccctgttt ctaatggaga   1860
ccaaactctc gctcagtgcc agaactctgt gtttgtcacc tgcgatgttt gtgctacacc   1920
agccactctc atcttgccct tcaccaatac cacatggcgt aaaagcacac gtgaaaacta   1980
tggctatata acctggcatg ttgtgaatcg cctaacagtt aactcaacat ctccatctac   2040
aatcagctgt gtcattctga tgcgagttgg taaggatttt cagtttacag ctcccctgta   2100
tggggccctg cagatggctg ccaataacca gggtgattcc aatcagcttg gcgatgatga   2160
accagtgtgt tttctcaatt ttgagactgc aaatgtgcca atacaagggg agtcacacac   2220
tttggtgaaa catctttttg gtcgtcaatg gctggttcgt actgttcaac atactagtga   2280
ggtacaagag ttggatttgc cagtacctga ccagggtcac gcatctctat tgcgcttctt   2340
tgcctacttc tctggagaag tgattttgac cattgtcaat aatggaacaa caccatgcat   2400
ggttgcacac tcttacacaa tggacaatct cacttctgaa tatgctgtca cagccatggg   2460
gggtattctt atcccagcaa actctgccaa gaatattaat attccattct attctgttac   2520
acctttacgc cccacacgac ccatgccagc atttcagggg ggtggtttga cttttggcag   2580
```

-continued

```
gttgtacatt tggacacaat caggaagtgt ttctgttttt atgggtctcc acaagccagc   2640
tttgtttttt ccactgcctg caccaactta cacaacacat acacagttga ataatattga   2700
aaccatgaat ctgcataatc aatcagatca gccagattgc cacctgtgta agatttgtaa   2760
gaaaatgaag aaatggtctc gcaaccatcg cccatttcgc ttctgtttga gacttaaaac   2820
acttgccttt gagctccatc tagaaattga atcagaccaa tctcgaaatg tcagagacct   2880
cactactgag ggtgttgagc ccaacccagg ccccattatg gttgttggta aatcaggatc   2940
tggcaaaagt gcattgtgta acatattggc tgatgtaaac cttttcgagt ctaaattaac   3000
tccttataca ctcacaacaa cgcatcagat tgaaactgtg actatctgtg acaagcaagt   3060
gaccctaatt gacacaccag aaataccaaa atatgatgga ccaattactt gtttccttta   3120
cctcattgaa gctggccgct ttactaatga ggatgttatt tttatgaaga caatgaggca   3180
atatttccct ggttttgaaa aatctaccat tttggtttta aatagggctg atgaattact   3240
caataatgat cagctcaagg actggattaa aactaatgga gaattagaat cacttgttcg   3300
tgcctgtgat ggccgggttg ccaaatttta tcgtggtaag attgccacta gcaagctttt   3360
ggataaaatt gcagagttgc ctgagtatcg tgctcactta ccgaggttgg ttcacaaaga   3420
tagaaaaatg tatcgtcatt atggtgtgca gtgtggcaat attgtgttcc acatggattc   3480
tgagaatata atgaaatctg cactcaatgg agaggtcacc atcaaacaag agaagtggaa   3540
tggcaattgg aaacctgcca gtgagcacat gcaaagcaca gcatcaatct atttaaaatc   3600
tgacacaatg ccaaaattta gattttctgt tgatgataat tgtgaaactt gggcaagaca   3660
attgctgggt gattatggtc ccacacaggg aacaatcttg aaagagcgtc ttatgtgggc   3720
tgcagcattg ggtttttta tgacaatgaa aattacaact gaccaatcat ttcctgggaa   3780
agatgctata cacactgttt tgaccaaaat ttctaatttt atttttggtg gtcttgaaaa   3840
tgaagtggtg agaattgtca ttcgcacggt gatacgcatt gtctgttatc taattttata   3900
tattcattca ccaaatattg ttaccacagg gacgttagtt gcattgcttg ccttagacgc   3960
cactagcatg agtatggacc agggcctcaa gactctctgt atgagtttgg ttgatgggga   4020
ttttggaaaa ttttgttcag tcttgttgca aaaaattcaa tccgttgatg gggctgacct   4080
taaaaacacc attcccttat tcacagatat gatggaagat caatcaggca aacccactgg   4140
tcctaagaca tttaatgatt ggaccacatg tgcaaaaaat gttcaatggt ggttagaatc   4200
ttttataaaa gttgtgaatt ggctaaaaga aaaagtattt ccatccaaga ctgaccctac   4260
tctacagtgg cttgaagatc atgaggagca tatttctatt atgttagcat tgtgtgatga   4320
acacttgtgc atgatccgga ctgataagga ctatatttgt gaacacacca ctcgtcctaa   4380
gcatcaaaaa ttagttgaga tggtttctaa cactttgaat caattaaatg gcatttccag   4440
tgctaaagat ttatgcttaa gattacagca tgtcttaaat aagctccacc aggtcaattt   4500
tgagccagaa ttggaatgga cacaccgacc cgaacctctt ggtatttgga tttcaggtgg   4560
gccgggtgtt gggaagagtt tcttatccaa ctatatagtc aaacaaatag caaagaaaag   4620
gcattggaag tcttatgcaa atccaacagg gtcaaagcat atggatgggt atgtttcaca   4680
ggaaattcat gtctttgatg attttggcca gaatcgtgaa gaggaggatt actctctcat   4740
ttgtaatttg atttctagtg ttccctttat aacaccaaaa gccagtgttg aagccaaagg   4800
cacccagtat cgtggcagac ttgtagtagt taccactaac aggagagatt tcacttcatg   4860
taaactcact gatcctgacg cgttagagcg taggtttcca atccgactta acattaggcc   4920
```

-continued

```
ccttcagaaa tataatcata aaggtaggtt ggatgtcgct actgcaatga gggatggcag   4980
tctgcagaat ggcacttgct gggagcgtga tattggtggg ttgggccttg aacactggaa   5040
cccaattaat ggagatacac ttatagatga gattctctca gagctgcagg ttagacagga   5100
agttgccagt tttatgaatc agggcaaggt gcgtaggcta agtgatttgg acacaatgtt   5160
tgaagaattg gatgaattaa aacttgattt tgattttgac cgcttggagg aacaggccag   5220
actcttcgcc cgcccaaagg aaggtaaaat ctccaaattt aggacctggg tgaaagaatg   5280
catcaataag attaaaggct ttcttgaacg taatagagct tggatacttg gaattggaac   5340
actcggcacc attgtgtccc tcataacaat gtgtattcca ttggctcgta aatttactca   5400
atctatctat tcaactcaac caatggctaa gactctacca aaagacttta aagtggcagt   5460
gcagaagcat gtagagaagc ttgaaagtgt gctccaggac cagggtggtc gtgtgaattt   5520
ccgccacata tgtaataggt tggtcaatgt ctctagtgaa aatgaagttg ccacaggatt   5580
ggcagttggt ggcaagtatg tcttaacttt tgggcattct aagtttactc aattggattc   5640
catcagagat atggtcttta attcaccggt taaaggaaca ccgattactt atgatgggct   5700
accaacagat ctccaactct tagattgtga tataccccac caatttaaag atgtgtctaa   5760
gctcatagct acagatgatt atcgaggcaa tggctggtta gtgtggaaag atgatgacca   5820
atatatgatt caagaggtta ctaaaatcag accctttgga caaactacaa ctgcttctgg   5880
cacaacatca tgccaaacat atatttataa ttgtaaaaca ggccctggtt catgtggtgg   5940
agtgcttgta gcccttgttg gaggaaacct aaaaattctt gggatccaca ccagtggtaa   6000
tggtacaatg ggtgcaagta atcgcatctt ccctgtgttt aatcaaggag ccattgttga   6060
gaaaaagtat tcaggaaaga tcctctatca ccagccccgt aagactgctt atcaaaaatc   6120
accagtttat gaggattctc cctatgaacc tgctgttctt tctatcaatg accagcgcct   6180
tgcagtacca attgaggata tggcaaagaa agctagtgac aaatatattg gaaatacatt   6240
tgccccacca ccaccagctt ttcaattggc aaaaacacat gtggctgaaa aattggctaa   6300
agtgctgggc tctcatggtt gtgtatctta tgagcaggcc atttctagtg atgtaatacc   6360
aatgaattgg gacacctctc caggaattaa gtataaaggt gagacaaagc gccagctggt   6420
gtgtaaatct tcttttaaac aggatgttat ggatcagatt cagtctccat ctacagtgtt   6480
tgtgtgttat ctcaaagatg agctacgtaa aaaggagaaa attaaggaag gaaagactcg   6540
aggtattgag gcatgcaact ttgactacac agttgcattt cgcatggtta tgggtgaaat   6600
ttattccaac atttatgatg atagctttat tttatcaggc tgtgctgttg gaatcaaccc   6660
ttttgctgag tgggacaatc tgttagcaaa tttgcagcct tacaacttgt gtttggactt   6720
ttctggtttt gacgggtctc tgagtgctca aattttggaa gaagctgttg atgtgttgtc   6780
attttttcac aacgatccag cccttgtgaa gaaaattcat gagccaacca tttattcgac   6840
acactatgtc actgatgaga tatggaaggt ggaaggcggt atgtgctcag gatcaccctg   6900
taccactgtc ctaaattcaa ttgtgaacca gctggcatgt tatactgtgc ttgctgtgtt   6960
gggctatgat atcaatcagt gttatgttgt cagctatgga gatgattgtg ttttgtctgt   7020
accggagaag cgggatatta gtaaactatc ccattatttt aaacttttct ttggtatgac   7080
agccacagcc agcgacaagg ctagtgacat agcatggagg ggcccaatgg aaattgagtt   7140
cttgaagaga acacctgcat ttctgcctga cactcgtaag atagttggag ttctggacaa   7200
ggaagttctt gaaggcaaga ttcagtggtg taaaggccca gaagcattta aacaacaatt   7260
ggattcattc tttctggaag ctgccttgca tggtcctgaa tattacaact acatttgttc   7320
```

-continued

```
caaattgaaa gctcgctgtc ctgttttgga aattcaacca tggggtgttg ccaggatgcg   7380
agcatatact gcctgcatga ttatataacc tgcaggcata gcagttccag ggtctgctg    7440
tagtcaatta aaacctggac tctttgtggt tatggggttt cccactcttg tttcaaaaac   7500
ctccctctag ggcgtagtgt tgtgggatac cctagagtac acgtaaaaca cccaccggtt   7560
tggcaggaca ccgcagagga actgcccagt gttggtccta ctgtctgaac aggactatct   7620
tagagtagtt atactaatca attccccgtc taggttgatt tagttagtat ttagtataag   7680
accaatggtg atataaagac cacacctaat ctccattttc ggtgtgtgac cctaagccat   7740
tggacttctt tactttacta ttcctcccca ccctaaaaaa aaaaaaaa                7788
```

<210> SEQ ID NO 27
<211> LENGTH: 7788
<212> TYPE: DNA
<213> ORGANISM: Duck hepatitis A virus

<400> SEQUENCE: 27

```
tttgaaagcg gctgtggtgt agaccatttt ctggcgcttg gttcagccag tatggtctca     60
ccacagtctg cttggggtta ttcccaaacc ccttaattca acgcctagtc ctagcgatat    120
aggactccct atccacttgt tttaccttta ccctccacta tatagtctgt tttctggcta    180
ttgactttgg ctttggtttt tgactcatgt ctaagtctct atagattttg tagtggttag    240
cctaccaccc cttggccact aattcttggc ttcttgtttt gggatccacc atatcttgga    300
ggtggtgctg aaatattgca agccacttgg tatgtgtgta ttttccaaac atgaagctct    360
ggtgcagtgg ttttggacaa ggaaaggcta gtgtttggtc tggatatgaa ctcttgttgt    420
gaaacggatt accggtagta gcatctagtg gttccagtcc ataacatgag tgtatggtct    480
agagtggaca tagcttggat acagacacct tcagtattac tgggtgttcc agactagttc    540
ctgaggtacc aagttatgag gggatatggg aaaacccctt tgatccacac tgcctgatag    600
ggtcgcggct ggtcgagtcc catacactat aaaaccagtt gattttcatg caatggatac    660
tctaactaaa aacattgaag atgaaactgt caagattatt ggatcctgtg ctgagaaggc    720
acaagaagca atctctggtc ttggagcagt tgagagtgtt gcttcaacta actctgtggt    780
tgctactgca aatgctacaa caacacaaac aattcctgat ccaacagatg gttccacaga    840
tgacttttat tcatgttcct atgaggttgg ggcccagggt gacaacatct cacgtttagt    900
ccatctacac actggacagt ggtccacaca gcatggtgtt actacatgcc ttagatggtt    960
ggtcactcct ggatgttttt atacagttaa tacccaacca gcatatggac aaaccaggta   1020
ttttaggttc atcagatgtg gctaccactt ccgccttctt gtgaatgcac catctggtgc   1080
tgctggtgga ctaatgatgg tgtggatgcc ttatccatat tgccgggttc tcactggatc   1140
ttacaatgtg gatgcatcag tagatcgcag gtcgttgtta aatcttccct atgccatctt   1200
ggatctgcgc accaacactg aaattgactt ggttattcca tatgtaaatt ttagaaatta   1260
tgttgaaatt actgccacag atagtgttgg tggggccata tgtgtctttg tgttgggagc   1320
ttatacacat gggtcaggaa cctccaatac tgttgattat actctctttg gtgagatgct   1380
tgaaactgac ttacaatgtc ctcggccttt taatgaccag ggtaagaaga aaccacggcg   1440
gaggccaatt cataaaccaa agagccctcc tcaagaatct cgcatcatta ttcagcctgg   1500
accaggagct gcaaatctat ccaattctag tgtggttacc atggctgaga gtgtggctct   1560
agctaatgag ggtactgcag ttgactactc aacagctggg tgtgcatcgt ctgtggatga   1620
```

-continued

```
tgtagtcatg gtgcttagac gctggcagat tgtgggtgat tttcagtggg ctaacacagt   1680
gacccctggc aatagaattg ataggtttca ggtggttttc aatcgtatgc caacctttgc   1740
tctctttttt gataagttcc agtattggag ggggtccctg gaggttaaat tattgacctt   1800
tggaagccag tttaatactg gccgctatca gatgtcatgg taccctgttt ctaatggaga   1860
ccaaactctc gctcagtgcc agaactctgt gtttgtcacc tgcgatgttt gtgctacacc   1920
agccactctc atcttgccct tcaccaatac cacatggcgt aaaagcacac gtgaaaacta   1980
tggctatata acctggcatg ttgtgaatcg cctaacagtt aactcaacat ctccatctac   2040
aatcagctgt gtcattctga tgcgagttgg taaggatttt cagtttacag ctcccctgta   2100
tggggccctg cagatggctg ccaataacca gggtgattcc aatcagcttg gcgatgatga   2160
accagtgtgt tttctcaatt ttgagactgc aaatgtgcca atacaagggg agtcacacac   2220
tttggtgaaa catctttttg gtcgtcaatg gctggttcgt actgttcaac atactagtga   2280
ggtacaagag ttggatttgc cagtacctga ccagggtcac gcatctctat tgcgcttctt   2340
tgcctacttc tctggagaag tgattttgac cattgtcaat aatggaacaa caccatgcat   2400
ggttgcacac tcttacacaa tggacaatct cacttctgaa tatgctgtca cagccatggg   2460
gggtattctt atcccagcaa actctgccaa gaatattaat attccattct attctgttac   2520
acctttacgc cccacacgac ccatgccagc atttcagggg ggtggtttga cttttggcag   2580
gttgtacatt tggacacaat caggaagtgt ttctgttttt atgggtctcc acaagccagc   2640
tttgtttttt ccactgcctg caccaactta cacaacacat acacagttga ataatattga   2700
aaccatgaat ctgcataatc aatcagatca gccagattgc cacctgtgta agatttgtaa   2760
gaaaatgaag aaatggtctc gcaaccatcg cccatttcgc ttctgtttga gacttaaaac   2820
acttgccttt gagctccatc tagaaattga atcagaccaa tctcgaaatg tcagagacct   2880
cactactgag ggtgttgagc ccaacccagg ccccattatg gttgttggta aatcaggatc   2940
tggcaaaagt gcattgtgta acatattggc tgatgtaaac cttttcgagt ctaaattaac   3000
tccttataca ctcacaacaa cgcatcagat tgaaactgtg actatctgtg acaagcaagt   3060
gaccctaatt gacacaccag aaataccaaa atatgatgga ccaattactt gtttccttta   3120
cctcattgaa gctggccgct ttactaatga ggatgttatt tttatgaaga caatgaggca   3180
atatttccct ggttttgaaa aatctaccat tttggtttta aatagggctg atgaattact   3240
caataatgat cagctcaagg actggattaa aactaatgga gaattagaat cacttgttcg   3300
tgcctgtgat ggccgggttg ccaaatttta tcgtggtaag attgccacta gcaagctttt   3360
ggataaaatt gcagagttgc ctgagtatcg tgctcactta ccgaggttgg ttcacaaaga   3420
tagaaaaatg tatcgtcatt atggtgtgca gtgtggcaat attgtgttcc acatggattc   3480
tgagaatata atgaaatctg cactcaatgg agaggtcacc atcaaacaag agaagtggaa   3540
tggcaattgg aaacctgcca gtgagcacat gcaaagcaca gcatcaatct atttaaaatc   3600
tgacacaatg ccaaaattta gattttctgt tgatgataat tgtgaaactt gggcaagaca   3660
attgctgggt gattatggtc ccacacaggg aacaatcttg aaagagcgtc ttatgtgggc   3720
tgcagcattg ggtttttttta tgacaatgaa aattacaact gaccaatcat ttcctgggaa   3780
agatgctata cacactgttt tgaccaaaat ttctaatttt atttttggtg gtcttgaaaa   3840
tgaagtggtg agaattgtca ttcgcacggt gatacgcatt gtctgttatc taattttata   3900
tattcattca ccaaatattg ttaccacagg gacgttagtt gcattgcttg ccttagacgc   3960
cactagcatg agtatggacc agggcctcaa gactctctgt atgagtttgg ttgatgggga   4020
```

-continued

```
ttttggaaaa ttttgttcag tcttgttgca aaaaattcaa tccgttgatg ggctgacct   4080
taaaaacacc attcccttat tcacagatat gatggaagat caatcaggca aacccactgg   4140
tcctaagaca tttaatgatt ggaccacatg tgcaaaaaat gttcaatggt ggttagaatc   4200
ttttataaaa gttgtgaatt ggctaaaaga aaaagtattt ccatccaaga ctgaccctac   4260
tctacagtgg cttgaagatc atgaggagca tatttctatt atgttagcat tgtgtgatga   4320
acacttgtgc atgctccgga ctgataagga ctatatttgt gaacacacca ctcgtcctaa   4380
gcatcaaaaa ttagttgaga tggtttctaa cactttgaat caattaaatg gcatttccag   4440
tgctaaagat ttatgcttaa gattacagca tgtcttaaat aagctccacc aggtcaattt   4500
tgagccagaa ttggaatgga cacaccgacc cgaacctctt ggtatttgga tttcaggtgg   4560
gccgggtgtt gggaagagtt tcttatccaa ctatatagtc aaacaaatag caaagaaaag   4620
gcattggaag tcttatgcaa atccaacagg gtcaaagcat atggatgggt atgtttcaca   4680
ggaaattcat gtctttgatg attttggcca gaatcgtgaa gaggaggatt actctctcat   4740
ttgtaatttg atttctagtg ttccctttat aacaccaaaa gccagtgttg aagccaaagg   4800
cacccagtat cgtggcagac ttgtagtagt taccactaac aggagagatt tcacttcatg   4860
taaactcact gatcctgacg cgttagagcg taggtttcca atccgactta acattaggcc   4920
ccttcagaaa tataatcata aaggtaggtt ggatgtcgct actgcaatga gggatggcag   4980
tctgcagaat ggcacttgct gggagcgtga tattggtggg ttgggccttg aacactggaa   5040
cccaattaat ggagatacac ttatagatga gattctctca gagctgcagg ttagacagga   5100
agttgccagt tttatgaatc agggcaaggt gcgtaggcta agtgatttgg acacaatgtt   5160
tgaagaattg gatgaattaa aacttgattt tgattttgac cgcttggagg aacaggccag   5220
actcttcgcc cgcccaaagg aaggtaaaat ctccaaattt aggacctggg tgaaagaatg   5280
catcaataag attaaaggct ttcttgaacg taatagagct tggatacttg gaattggaac   5340
actcggcacc attgtgtccc tcataacaat gtgtattcca ttggctcgta aatttactca   5400
atctatctat tcaactcaac caatggctaa gactctacca aaagacttta aagtggcagt   5460
gcagaagcat gtagagaagc ttgaaagtgt gctccaggac cagggtggtc gtgtgaattt   5520
ccgccacata tgtaataggt tggtcaatgt ctctagtgaa aatgaagttg ccacaggatt   5580
ggcagttggt ggcaagtatg tcttaacttt tgggcattct aagtttactc aattggattc   5640
catcagagat atggtcttta attcaccggt taaaggaaca ccgattactt atgatgggct   5700
accaacagat ctccaactct tagattgtga tataccccac caatttaaag atgtgtctaa   5760
gctcatagct acagatgatt atcgaggcaa tggctggtta gtgtggaaag atgatgacca   5820
atatatgatt caagaggtta ctaaaatcag accctttgga caaactacaa ctgcttctgg   5880
cacaacatca tgccaaacat atatttataa ttgtaaaaca ggccctggtt catgtggtgg   5940
agtgcttgta gcccttgttg gaggaaacct aaaaattctt gggatccaca ccagtggtaa   6000
tggtacaatg ggtgcaagta atcgcatctt ccctgtgttt aatcaaggag ccattgttga   6060
gaaaaagtat tcaggaaaga tcctctatca ccagccccgt aagactgctt atcaaaaatc   6120
accagtttat gaggattctc cctatgaacc tgctgttctt tctatcaatg accagcgcct   6180
tgcagtacca attgaggata tggcaaagaa agctagtgac aaatatattg gaaatacatt   6240
tgccccacca ccaccagctt ttcaattggc aaaaacacat gtggctgaaa aattggctaa   6300
agtgctgggc tctcatggtt gtgtatctta tgagcaggcc atttctagtg atgtaatacc   6360
```

-continued

```
aatgaattgg gacacctctc caggaattaa gtataaaggt gagacaaagc gccagctggt   6420
gtgtaaatct tcttttaaac aggatgttat ggatcagatt cagtctccat ctacagtgtt   6480
tgtgtgttat ctcaaagatg agctacgtaa aaaggagaaa attaaggaag gaaagactcg   6540
aggtattgag gcatgcaact ttgactacac agttgcattt cgcatggtta tgggtgaaat   6600
ttattccaac atttatgatg atagctttat tttatcaggc tgtgctgttg gaatcaaccc   6660
ttttgctgag tgggacaatc tgttagcaaa tttgcagcct tacaacttgt gtttggactt   6720
ttctggtttt gacgggtctc tgagtgctca aattttggaa gaagctgttg atgtgttgtc   6780
attttttcac aacgatccag cccttgtgaa gaaaattcat gagccaacca tttattcgac   6840
acactatgtc actgatgaga tatggaaggt ggaaggcggt atgtgctcag gatcaccctg   6900
taccactgtc ctaaattcaa ttgtgaacca gctggcatgt tatactgtgc ttgctgtgtt   6960
gggctatgat atcaatcagt gttatgttgt cagctatgga gatgattgtg ttttgtctgt   7020
accggagaag cgggatatta gtaaactatc ccattatttt aaacttttct ttggtatgac   7080
agccacagcc agcgacaagg ctagtgacat agcatggagg ggcccaatgg aaattgagtt   7140
cttgaagaga acacctgcat ttctgcctga cactcgtaag atagttggag ttctggacaa   7200
ggaagttctt gaaggcaaga ttcagtggtg taaaggccca gaagcattta aacaacaatt   7260
ggattcattc tttctggaag ctgccttgca tggtcctgaa tattacaact acatttgttc   7320
caaattgaaa gctcgctgtc ctgttttgga aattcaacca tggggtgttg ccaggatgcg   7380
agcatatact gcctgcatga ttatataacc tgcaggcata gcagttccag gggtctgctg   7440
tagtcaatta aaacctggac tctttgtggt tatggggttt cccactcttg tttcaaaaac   7500
ctccctctag ggcgtagtgt tgtgggatac cctagagtac acgtaaaaca cccaccggtt   7560
tggcaggaca ccgcagagga actgcccagt gttggtccta ctgtctgaac aggactatct   7620
tagagtagtt atactaatca attccccgtc taggttgatt tagttagtat ttagtataag   7680
accaatggtg atataaagac cacacctaat ctccattttc ggtgtgtgac cctaagccat   7740
tggacttctt tactttacta ttcctcccca ccctaaaaaa aaaaaaaa                7788
```

DUCK HEPATITIS A VIRUS TYPE 3 MUTANT CH-P60-117C AND CONSTRUCTION THEREOF

CROSS-REFERENCE TO RELATED APPLICATIONS

This application is a continuation of International Patent Application No. PCT/CN2019/125293, filed on Dec. 13, 2019, which claims the benefit of priority from Chinese Patent Application No. 201910551115.2, filed on Jun. 24, 2019. The content of the aforementioned application, including any intervening amendments thereto, is incorporated herein by reference in its entirety.

TECHNICAL FIELD

The disclosure relates to genetic engineering, and more specifically to a duck hepatitis A virus type 3 (DHAV-3) mutant CH-P60-117C and a construction method for DHAV-3.

BACKGROUND

Duck viral hepatitis (DVH) is an acute and highly contagious infectious disease in ducklings caused by duck hepatitis virus (DHV). At present, this disease occurs in all the major duck-raising regions worldwide, and has the characteristics of intermittent outbreaks and local epidemics. It is one of the major diseases that threaten the duck-breeding industry. This disease mainly occurs in ducklings within four weeks old, and is characterized by acute onset, rapid transmission, short course of disease and high mortality, etc. The main clinical manifestation is that the duckling suffers from a spasm before death with its head tilting backward towards the back to show opisthotonus. The pathological changes observed by dissection mainly include visible liver swelling and inflammation and a large number of hemorrhagic spots. This disease is mainly caused by duck hepatitis A virus (DHAV), which pertains to the genus *Avihepadnavirus* of family Picornaviridae. DHAV has three serotypes, respectively DHAV-1, DHAV-2 and DHAV-3, and in recent years, the DHAV prevalent in China are mainly DHAV-1 and DHAV-3.

Reverse genetics (RG) technique plays an important role in carrying out researches in virus molecular biology, which enables the in-vitro manual operation on the genome of RNA viruses such as gene knockout and site-directed mutagenesis. It also plays an important role in elucidating the pathogenic mechanism of virus and developing vaccines, and is superior to the natural mutagenesis in the mutagenesis period. The key to the traditional infectious clone of the RNA virus is to obtain the full-length clones of the viral genome cDNA, and after the viral genome is converted to cDNA, it is still needed to clone the cDNA into a suitable vector. To overcome the instability of the viral sequences in bacteria, a fragmentation cloning method is generally adopted, in which the small fragments are ligated into a large fragment, which is then subjected to enzyme digestion and ligation to finally obtain the full-length cDNA clone. However, this method is largely restricted in the selection of enzyme cleavage sites, and the in vitro ligation of multiple large fragments generally has relatively low efficiency. In addition, cDNA clones of some viral genes related to viral replication are unstable in bacteria. Therefore, the whole process of obtaining full-length cDNA of the viral genome not only has complicated and time-consuming operation, but also has a low success rate. Meanwhile, the full-length cDNA of some viruses can not be cloned, or although they can be cloned into vectors, they are susceptible to mutations in the host bacteria and can not successfully rescue the virus. Currently, a technique named "infectious subgenomic amplicons" has been proven to enable the artificial rescue of single positive-stranded RNA virus in mammalian or mosquito cells, and has been applied to the reverse genetics studies of Japanese encephalitis virus, West Nile virus, Zika virus, yellow fever virus, dengue virus, and human Coxsackie virus. The technique is a novel "bacteria-free" reverse genetics method, in which the rescue of viruses can be completed through the direct transfection with DNA fragments with homologous regions without the need to obtain the full-length cDNA plasmid of the virus or the viral RNA transcripts in vitro. Specifically, in the "infectious subgenomic amplicon" technique, multiple overlapping non-infectious subgenomic DNA fragments containing the entire viral genome are produced by PCR, where the number of these overlapping subgenomic amplicons can be 3 to 10 and there is an about 100 bp overlapping region between the adjacent amplicons; meanwhile, the 5' end of the first fragment and the 3' end of the last fragment are respectively laterally ligated with the cytomegalovirus immediate early promoter (pCMV) sequence, hepatitis delta virus ribozyme (HDVR) sequence and SV40 early mRNA polyadenylation signal (SV40 pA) sequence, where these elements facilitate the transcription of subgenomic amplicons and the spontaneous recombination using the homologous recombination mechanism of the host cells, to form a complete infectious viral transcript, resulting in the replication and proliferation of the virus and finally obtaining the infectious rescued virus.

Currently, the prevention and control of DHAV is performed mainly using a commercially-available DHAV-1 attenuated vaccine, and there is still a lack of high-efficient DHAV-3 live vaccine. Therefore, there is an urgent need to develop a new molecular marker vaccine suitable for the epidemic situation of DHAV-3 in China. Meanwhile, the basic researches on viral genes and key sites related to host tropism and virulence changes of DHAV can provide a theoretical reference for the prevention and treatment of duck hepatitis, while in such researches, it is also urgently required to obtain the virus strains with host tropism and changed virulence.

SUMMARY

An object of the disclosure is to obtain a candidate virus strain of DHAV-3 vaccine through genetic modification, where the virus strain with host tropism and changed virulence can be used in the basic researches on viral genes and key sites related to host tropism and virulence change of DHAV.

To achieve these technical objects, the disclosure adopts the following technical solutions.

In a first aspect, the present disclosure provides a mutant of DHAV-3 CH-P60-117C (DHAV-3 CH-P60-117C), wherein the DHAV-3 mutant CH-P60-117C is obtained by mutating A at position 117 of 5'-UTR of genome of the DHAV-3 virulent strain to C, mutating T at position 1142 to A to mutate tyrosine-164 of the VP0 protein of the DHAV-3 virulent strain to asparagine, and mutating C at position 4334 to A so that leucine-71 of protein 2C of the DHAV-3 virulent strain is mutated to isoleucine.

The DHAV-3 mutant CH-P60-117C is deposited in the China Center for Type Culture Collection (CCTCC, College of Life Sciences, Wuhan University, Wuhan, China, 430072) on Dec. 2, 2018 with an accession number of CCTCC NO: V201860, and its gene sequence is shown in SEQ ID NO: 26.

The DHAV-3 virulent strain is deposited in the China Center for Type Culture Collection (CCTCC, College of Life Sciences, Wuhan University, Wuhan, China, 430072) with an accession number of CCTCC NO: V201305, and its gene sequence is shown in SEQ ID NO: 27.

In an embodiment, G at position 3403 of genome of the DHAV-3 mutant CH-P60-117C is mutated to T as a genetic marker of infectious clones, so that the DHAV-3 mutant CH-P60-117C can be distinguished from the parent strain and the wild virulent strain by PCR in combination with DNA sequencing.

The mutant strain with the genetic marker in the disclosure can undergo stable proliferation and passage in the 9-day-old duck embryos like the parent virus, and has higher virus titer. Moreover, the mutant strain can also undergo stable proliferation and passage in 9-day-old chicken embryos, and no mutation is observed in consecutive 10 passages, showing good genetic stability.

Compared to the parent strain, the mutant with the genetic marker shows significantly reduced pathogenicity to ducklings, which can successfully replicate in ducklings.

In a second aspect, the disclosure provides a method of preparing a DHAV-3 vaccine, comprising:

inoculating the DHAV-3 mutant CH-P60-117C of claim 1 into duck embryos through allantoic cavity;

incubating the duck embryos;

collecting and cooling the duck embryos that die;

aseptically collecting an allantoic fluid from the duck embryos;

treating the allantoic fluid with a formaldehyde solution and incubating the allantoic fluid at 37° C. for 24 h to inactivate the DHAV-3 mutant CH-P60-117C;

diluting the allantoic fluid; and emulsifying the diluted allantoic fluid with an adjuvant to produce the DHAV-3 vaccine.

At the same time, the mutant strain can also be used in basic research on genes and key sites related to host tropism and virulence of duck hepatitis viruses.

In a third aspect, the disclosure provides a method for constructing the DHAV-3 mutant CH-P60-117C, comprising:

(1) dividing the genome of the parent virus into a first fragment, a second fragment, and a third fragment (2.6 kb, 2.6 kb, and 2.7 kb) of similar size and amplifying the first fragment, the second fragment and the third fragment through PCR; adding a cytomegalovirus immediate early promoter (pCMV) to 5' end of the first fragment and introducing a first mutation site and a second mutation site respectively in the 5'-UTR gene and VP0 gene of the first fragment, introducing a third mutation site in the 2C gene of the second fragment and introducing a nonsense mutation in 2A gene of the second fragment as a genetic marker site, adding hepatitis delta virus ribozyme (HDVR) sequence and SV40 early mRNA polyadenylation signal (SV40 pA) sequence to the 3' end of the third fragment to construct an infectious subgenomic replicon of the DHAV-3 mutant CH-P60-117C; and (2) mixing the infectious subgenomic replicon of the DHAV-3 mutant CH-P60-117C with a transfection reagent followed by transfection into duck embryo fibroblasts; wherein the infectious subgenomic replicon is transcribed in the duck embryo fibroblasts and undergoes spontaneously recombination using a homologous recombination mechanism of the duck embryo fiberblasts to form an infectious complete virus transcript, thereby leading to replication and proliferation of virus to finally obtain the DHAV-3 mutant CH-P60-117C with a genetic marker.

In an embodiment, there is a 74 bp overlapping region between the first fragment and the second fragment, and a 83 bp overlapping region between the third fragment and the second fragment.

The beneficial effects of the disclosure are described as follows.

1. The method provided herein for constructing DHAV-3 mutant strain is superior to the natural mutagenesis and traditional reverse genetics technique due to the shorter experimental period, facilitating accelerating the development of DHAV-3 attenuated vaccine and the research on viral pathogenic mechanisms.

2. The mutant strain CH-P60-117C obtained in the disclosure has similar antigenicity to its parent strain and can maintain stable genetic characteristics during successive passages, therefore, this mutant strain can be used as a candidate vaccine strain of duck hepatitis A virus type 3. At the same time, it has higher proliferation efficiency and virus titer in duck embryos than the parent strain and wider sources of materials for culture, which can proliferate in chicken embryos. Therefore, the mutant strain CH-P60-117C may allow for increased production and reduced cost in the vaccine production.

3. The mutant strain CH-P60-117C obtained in the disclosure has similar antigenicity to its parent strain, and thus it can be used as a candidate DHAV-3 vaccine strain for the preparation of DHAV-3 vaccine.

4. The mutant strain CH-P60-117C obtained in the disclosure can replicate in ducklings but shows no pathogenicity to the ducklings, which indicates that the mutant strain has good safety, and thus it can be used as a candidate strain of attenuated vaccine for DHAV-3.

5. Compared to the parent strain, the mutant strain CH-P60-117C obtained in the disclosure has reduced virulence and can proliferate in chicken embryos, so it can be used in the study of genes and key sites related to host tropism and virulence changes of duck hepatitis viruses.

DETAILED DESCRIPTION OF EMBODIMENTS

Figure 1:
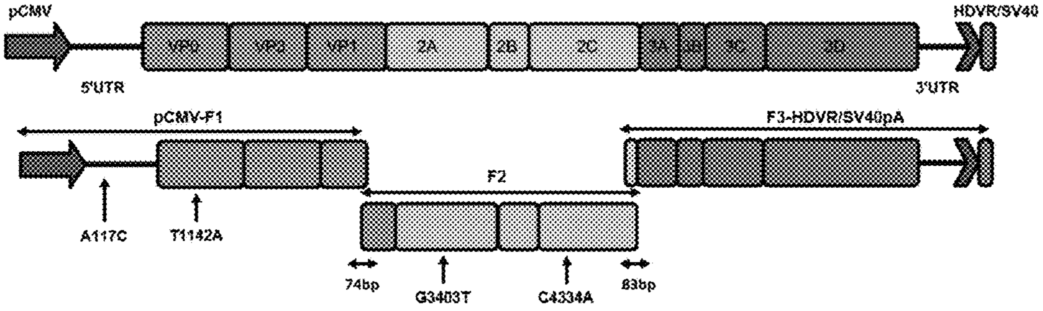
FIG. 1 schematically shows the construction of "infectious subgenomic replicons" of mutant strain CH-P60-117C with molecular marker based on DHAV-3.

The disclosure will be further described in detail below with reference to the embodiments, but is not limited thereto. Unless otherwise specified, the experimental methods used below all are conventional methods, and the experimental materials are all commercially available.

Materials and reagents used in the following examples are described as follows.

Virus Strain

DHAV-3 virulent strain: isolated by our laboratory and deposited in the China Center for Type Culture Collection at Wuhan University (China) with an accession number of CCTCC NO: V201305; classification: Duck Hepatitis A Virus type 3 (DHAV-3), *Picornavirus, Avihepadnavirus.*

Reagents and Instruments

TaKaRa MiniBEST Universal RNA Extraction kit, PrimeSTAR Max DNA Polymerase, DNA Marker, etc. were purchased from Takara Biomedical Technology (Dalian) Co., Ltd; E.Z.N.A.® Gel Extraction kit and E.Z.N.A.® Plasmid Purification kit were purchased from Omega Bio-Tek, Inc. (U.S.); Lipofectamine 3000 Transfection kit was purchased from Invitrogen, and other reagents are all analytical grade reagents made in China.

Nucleic Acid Protein Detector (Bio Rad, Smartspec 3000), Gradient PCR Instrument (Biometra, Tgradient), Electrophoresis Apparatus (Bio Rad, Powerpac 300), and Gel Imaging System (Bio Rad Versa Doc Model 2000) were used herein.

Example 1 Construction of "Infectious Subgenomic Replicon" of DHAV-3 Mutant Strain CH-P60-117C and Rescue of Virus 1.1 Design and Synthesis of Primers Based on the complete genome sequence of DHAV-3 in GenBank, nine pairs of primers were designed to amplify the complete genome sequence of DHAV-3, pCMV sequence and SV40 pA sequence, and the specific primer information was shown in Table 1. The primers were synthesized by Sangon Biotech (Shanghai) Co., Ltd.

TABLE 1

Construction of primes of infectious subgenomic replicon of DHAV-3 mutant strain CH-P60-117C

| Primer | Sequence 5'-3' | Note |
|---|---|---|
| pCMV-F | **TAGTTATTAATAGTAATCAATTACGGGGTCA** (SEQ ID NO: 1) | The sequence in bold was pCMV sequence |
| pCMV-R | ACACCACAGCCGCTTTCAA**ACGGTTCACTAAA CCAGCTCT** (SEQ ID NO: 2) | |
| F1-F | **AGAGCTGGTTTAGTGAACCGT**TTGAAAGCGGCTGTGGTGT (SEQ ID NO: 3) | |
| A117C-F | GCCTAGTCCTAGCG**C**TATAGGACTCCC (SEQ ID NO: 4) | The base in bold was the mutation site |
| A117C-R | GGGAGTCCTATA**G**CGCTAGGACTAGGC (SEQ ID NO: 5) | |
| F1-R | CAACCTGCCAAAAGTCAAACCA (SEQ ID NO: 6) | |
| T1142A-F | TCACTGGATCT**A**ACAATGTGGATGC (SEQ ID NO: 7) | The base in bold was the mutation site |
| T1142A-R | GCATCCACATTGT**T**AGATCCAGTGA (SEQ ID NO: 8) | |
| F2-1-F | ATTCTGTTACACCTTTACGCCCCACA (SEQ ID NO: 9) | The base in bold was Bln I enzyme site |
| F2-1-R | CAACC**T**AGGTAAGTGAGCACGAT (SEQ ID NO: 10) | |
| F2-2-F | GTGCTCACTTACC**T**AGGTTGGTT (SEQ ID NO: 11) | The base in bold was the genetic marker site |
| F2-2-R | TGGCAACTTCCTGTCTAACCTG (SEQ ID NO: 12) | |
| C4334A-F | ACTTGTGCATG**A**TCCGGACTGATAA (SEQ ID NO: 13) | The base in bold was the mutation site |
| C4334A-R | TTATCAGTCCGGA**T**CATGCACAAGT (SEQ ID NO: 14) | |
| F3-HDVR-F | CCTTGAACACTGGAACCCAA (SEQ ID NO: 15) | |
| F3-HDVR-R | **AAGTAGCCCAGGTCGGACCGCGAGGAGGTGGAGATGCCATGCCGACCC**TTTTTTTTTTTTTAGGGTGG (SEQ ID NO: 16) | The sequence in bold was HDVR sequence |
| HDVR-SV40pA-F | **CGGTCCGACCTGGGCTACTTCGGTAGGCTAAGGGAGAAG**AACTTGTTTATTGCAGCTTA (SEQ ID NO: 17) | |
| HDVR-SV40pA-R | TAAGATACATTGATGAGTTTGGA (SEQ ID NO: 18) | |

1.2 Extraction of Viruses

Following the instructions of TaKaRa MiniBEST Universal RNA Extraction kit, the whole genome RNA of DHAV-3 isolated strain was extracted from the duck embryo allantoic fluid, determined for the nucleic acid concentration and purity using a nucleic acid-protein detector (Bio Rad, Smartspec3000) and then stored at −70° C. for use.

1.3 Amplification and Cloning of Gene Fragments (1) The total extracted RNA was reverse transcribed into cDNA template using PrimeScript II 1$^{st}$ Strand cDNA Synthesis kit, and then fragments DHAV-3-F1-A117C, DHAV-3-F1-A117C-T1142A and DHAV-3-F1-T1142A were obtained via amplification using DNA high-fidelity PCR enzyme PrimeSTAR Max DNA Polymerase, primers F1-F and A117C-R, A117C-F and T1142A-R, T1142A-F and F1-R, and the reverse transcription product of the total RNA of parent strain virus as template. Fragments DHAV-3-F2-1, DHAV-3-F2-C4334A-1, and DHAV-3-F2-C4334A-2 were obtained via amplification using primers F2-1-F and F2-1-R, F2-2-F and C4334A-R, C4334A-F and F2-2-R, and the reverse transcription product of the total RNA of parent strain virus as template. Fragment DHAV-3-F3-HDVR was obtained via amplification using primers F3-HDVR-F and F3-HDVR-R, and the reverse transcription product of the total RNA of parent strain virus as template. In the use of an eukaryotic expression plasmid pEGFP-C1 as template, fragment pCMV was obtained via amplification using primers pCMV-F, pCMV-R and pCMV and fragment HDVR-SV40 pA was obtained via amplification using primers HDVR-SV40 pA-F and HDVR-SV40 pA-R.

(2) As shown in FIG. 1, fragments DHAV-3-F1-A117C, DHAV-3-F1-A117C-T1142A and DHAV-3-F1-T1142A were fused to form F1-A117C-T1142A by fusion PCR, and then the fragments pCMV and F1-A117C-T1142A were fused to form pCMV-F1. Fragments DHAV-3-F2-1, DHAV-3-F2-C4334A-1 and DHAV-3-F2-C4334A-2 were fused to form fragment F2. Fragments DHAV-3-F3-HDVR and HDVR-SV40 pA were fused to form fragment F3-HdvRz/SV40 pA. The fragments pCMV-F1, F2, and F3-HdvRz/SV40 pA together constituted an "infectious subgenomic replicon" of the mutant strain CH-P60-117C. After the amplified fragments were separated by 1% agarose gel electrophoresis, target fragments were respectively recovered by gel extraction using the Gel Extraction kit (Omega). The recovered DNA fragments were sequenced by Sangon Biotech (Shanghai) Co., Ltd.

Figure 2:
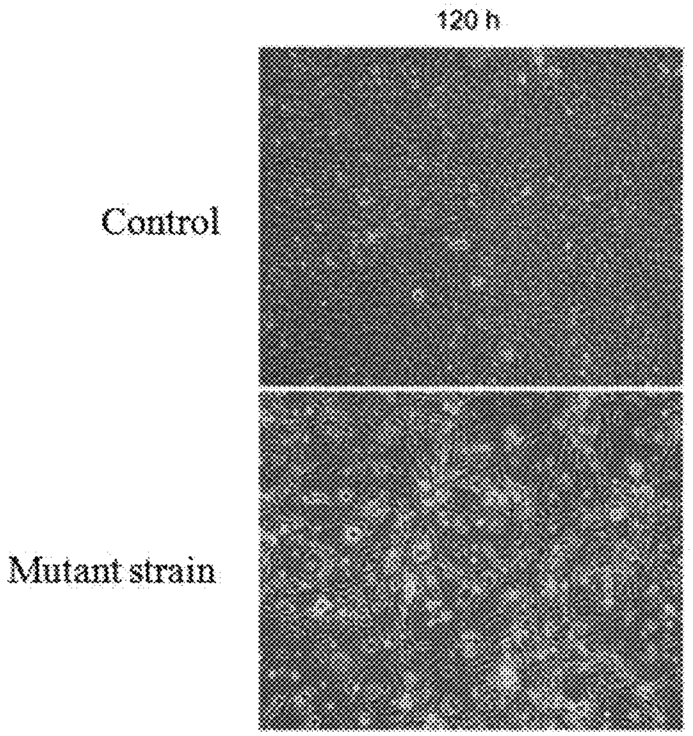
FIG. 2 shows the results of the transfection of duck embryo fibroblasts with "infectious subgenomic replicons" of DHAV-3 mutant strain CH-P60-117C.

1.4 Transfection Rescue of "Infectious Subgenomic Replicon" of Mutant Strain CH-P60-117C Primary duck embryo fibroblasts were prepared from 9-day-old duck embryos. When the cells grew to a confluency of 90% in the 3.5 cm culture dish, fragments pCMV-F1 (1.5 μg), F2 (1.5 μg) and F3-HdvRz-SV40 pA (1.5 μg) were mixed with Lipofectamine 3000 (Invitrogen) and transfected into the duck embryo fibroblasts with 90% confluency. Those fibroblasts only transfected with Lipofectamine 3000 (Invitrogen) were used as control. Cells were cultured and observed at 37° C. and 5% $CO_2$ in an incubator, and the medium was replaced after 16 h. 72 h after the transfection, a rupture was observed in the cells in the experimental group, while the cells in the control group showed good growth status. 120 h after transfection, the growth status of the cells was shown in FIG. 2. After recorded by photographing, the cells were subjected to repeated freezing and thawing 3 times, and the cell culture medium was inoculated into five duck embryos (0.2 mL each) aged 9 days through the allantoic cavity. The dish was sealed with paraffin, and then continuously incubated in the incubator. The cells were exposed to irradiation once every other 8 hours to observe the death of duck embryos after inoculation, and the duck embryos that died within 24 h were discarded. The results showed that the duck embryos died between 24 h and 48 h after the inoculation, and the dead duck embryos showed severe bleeding. The allantoic fluid was collected as the reverse genetic virus strain of the first passage for preservation.

Figure 3:
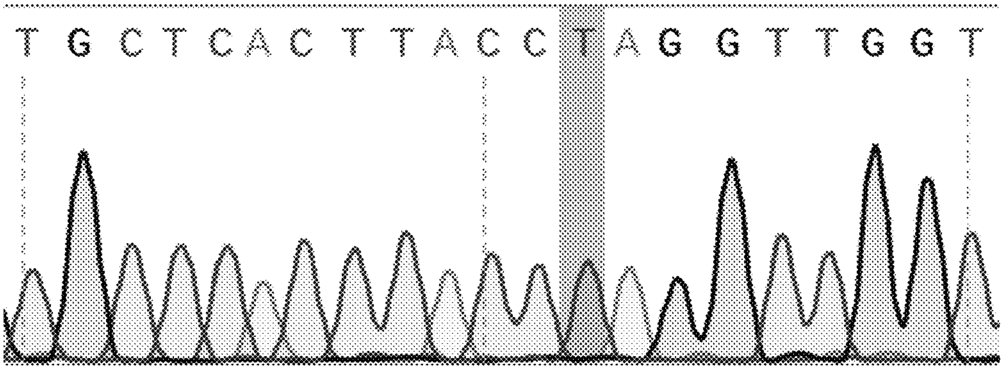
FIG. 3 shows the sequencing result (as shown in SEQ ID NO: 22) of the molecular genetic marker site at position 3403 of genome of the mutant strain CH-P60-117C.

Example 2 Identification and Characteristic Determination of DHAV-3 Mutant Strain CH-P60-117C 2.1 Identification of the Genetic Marker in the Rescued Virus To exclude the possibility that the rescued virus comes from the parental virus or wild virus strain due to the contamination during the transfection and passaging process, the base G at position 3403 of the mutant genome was mutated to T by reverse genetics method, and the mutation did not change the corresponding amino acid of the 2A protein. This mutation site was used as a molecular genetic marker site to enable the mutant strain to be distinguished from the parental strain and the wild strain through the combination of PCR and DNA sequencing. The rescued virus was passaged and purified 5 times on the duck embryo by limiting dilution assay. Total RNA was extracted from the allantoic fluid, and subjected to reverse transcription. The reverse transcription product was amplified to obtain DNA fragments containing mutation sites by PCR using F2-F and F2-R primers. The amplified fragments were separated by 1% agarose gel electrophoresis and then recovered by gel extraction using Gel Extraction kit (Omega). The DNA fragments were sequenced by Sangon Biotech (Shanghai) Co., Ltd. The sequencing results showed that the amplified product contained introduced silent mutation (G3403T), as shown in FIG. 3, further indicating that the desired rescued virus rather than the parental strain or the wild strain was obtained.

2.2 Detection of Genetic Stability of Rescued Virus and its Mutation Sites

Figure 4:
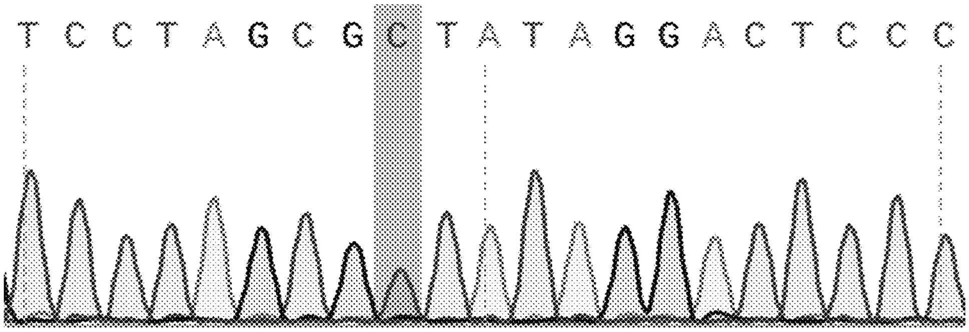
FIG. 4 shows the sequencing result (as shown in SEQ ID NO: 23) of the target mutation site at position 117 of genome of the mutant strain CH-P60-117C.
Figure 5:
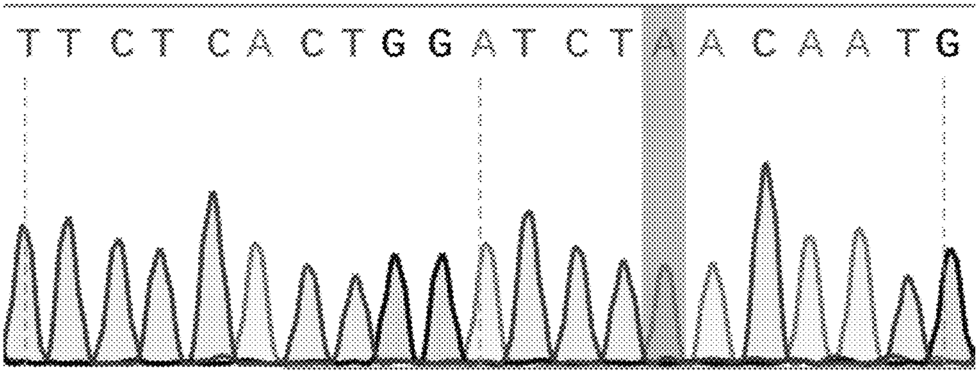
FIG. 5 shows the sequencing result (as shown in SEQ ID NO: 24) of the target mutation site at position 1142 of genome of the mutant strain CH-P60-117C.
Figure 6:
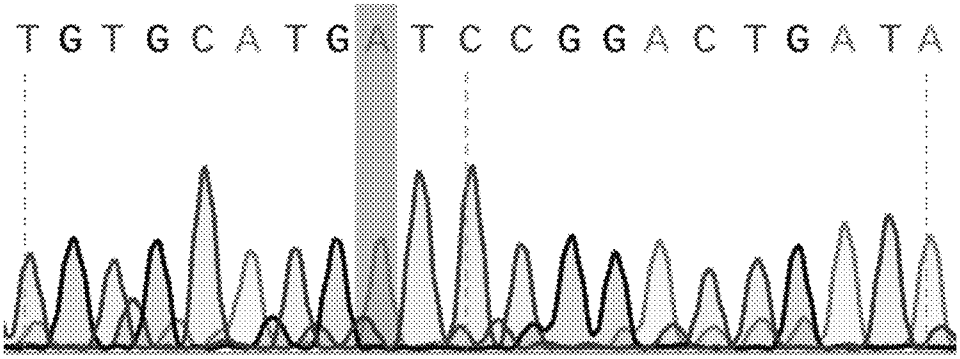
FIG. 6 shows the sequencing result (as shown in SEQ ID NO: 25) of the target mutation site at position 4334 of genome of the mutant strain CH-P60-117C.

To observe whether the rescued reverse genetic virus can undergo proliferation and passage in duck embryos and chicken embryos, the rescued virus of the first passage was diluted with sterilized saline in a ratio of 1:100 and inoculated into 5 duck embryos or chicken embryos aged 9 days. The results showed that the death of the duck embryos/chicken embryos mainly occurred between 24 h and 48 h after the inoculation, and obvious pathological changes were observed in the embryoid bodies. The viruses underwent successive 10 passages, and the virus fluid of each passage was collected and stored in a refrigerator at −80° C. The virus fluids from the viruses of the 1$^{st}$, 5$^{th}$, and 10$^{th}$ passages were subjected to RNA extraction and reverse transcription to produce cDNA, and then the DNA fragments containing the mutation sites were amplified through PCR, and the mutation sites and genetic marker sites were detected. As shown in FIGS. 4-6, the sequencing results showed that the viruses of the 1$^{st}$, 5$^{th}$, and 10$^{th}$ passage did not show mutations, indicating that the virus had good genetic stability.

2.3 Virus Proliferation and Content Determination

Sterilized saline was used in the serial 10-fold dilution of the rescued DHAV-3 and parental strain, and the virus suspensions with the dilution factor of $10^3$, $10^4$, $10^5$, $10^6$, $10^7$ and $10^8$ were respectively inoculated into 5 duck embryos aged 9 days in 0.2 mL per embryo through the allantoic cavity. 5 other embryos were inoculated with sterilized saline and used as control. After the inoculation, the embryos were all incubated at 37° C. in a constant-temperature incubator. The embryos which died within 24 h were not taken into account, and the death and survival of the inoculated embryos within 7 d were observed and recorded. ELD50 of the virus was calculated using Reed-Muech method, and the results showed that the rescued virus and the parental strain had different proliferative capabilities, specifically, the virus contents in 0.2 mL of allantoic fluids from the experimental group and the control group were $10^{-7.55}$ELD50 and $10^{-4.50}$ELD50, respectively, indicating that the mutant strain was superior to the parental strain in the proliferative capacity in duck embryos. Therefore, the mutant strain may facilitate the production increase and cost reduction when used in the production of antigens in vaccines.

In addition, the same experimental operation was also carried out on 9-day-old chicken embryos. The results showed that the DHAV-3 mutant strain CH-P60-117C can proliferate in chicken embryos and cause the death of the chicken embryos, and the virus titer of the mutant strain in the allantoic cavity fluid of the chicken embryos was $10^{-6.55}$ELD50; while the parental strain failed to proliferate in the chicken embryos and was not lethal to the chicken embryos. Given the above, the materials for culturing the mutant strain had wider sources, which will allow for reduced cost when the mutant strain was used in the production of antigens in vaccines. Moreover, the mutant strain was also different from the parental strain in the host tropism. Therefore, the mutant strain may be used as basic materials for the study of genes and key sites related to the host tropism and virulence change of duck hepatitis viruses.

2.4 Detection of Viral Antigenicity by Serum Neutralization Test

This experiment was performed to detect whether the reverse genetic strain produced mature progeny virions during the duck embryo passage and whether the virus antigenicity had changed. The neutralizing titer of rabbit anti-DHAV-3 serum against the mutant strain and the parental strain was determined by serum neutralization test. First, the rabbit anti-DHAV-3 standard serum (titer 1:128) previously prepared in the laboratory was subjected to a serial 2-fold dilution with sterilized saline to produce 9 diluted serums with a dilution degree from $2^{-1}$ to $2^{-9}$, and at the same time, the virus was diluted to a content of 200ELD50/0.2 mL. The diluted rabbit anti-DHAV-3 standard serums were respectively mixed with the diluted virus suspension in equal amount, added with 5% penicillin-streptomycin solution and placed in water bath at 37° C. for 1 h. Then the serum-virus mixtures were respectively inoculated into the allantoic cavity of five 9-day-old healthy duck embryos at 0.2 mL per embryo. Five 9-day-old healthy duck embryos inoculated with a mixture of healthy rabbit serum and virus were used as the negative serum control group, and five 9-day-old healthy duck embryos inoculated with a mixture of sterilized saline mixed and virus were used as blank control group. The duck embryos that died within 24 h were discarded, and the death and survival of the embryos within 7 d were observed and recorded, and then the neutralizing titer of rabbit anti-DHAV-3 standard serum against the virus was calculated.

The results showed that the rescued virus and the parental virus had similar antigenicity since the duck embryos in the negative serum control group and the blank control group all died between 24 h and 48 h after the inoculation. In the case of a serum dilution between $2^{-1}$ and $2^{-6}$, the duck embryos in the mutant strain neutralization group and parental strain neutralization group all survived; when the serum dilution reached $2^{-7}$, the protection of the duck embryo began to lose, as the dilution degree increased, the protection rate of the duck embryo decreased; the protection of the duck embryo was completely lost until the dilution was $2^{-9}$, indicating that the use of mutant strain in preparing vaccine antigens can also protect the embryo from the infection of DHAV-3.

2.5 Virulence and Safety Test for the Susceptible Ducklings

The parental strain and the mutant strain were both subjected to safety tests. The liver tissues of the dead duck embryos in step (2.3) were collected, homogenized, added with sterilized phosphate buffer solution at a volume ratio of 1:100, ground and repeatedly frozen and thawed 3 times. The resulting tissue suspension was centrifuged at 12,000×g for 10 min, the supernatant was filtered by 0.22 μm filter for removing bacteria. The filtrate was inoculated into 9-day-old duck embryos through the allantoic cavity for the determination of ELD50, and then the virus solution was diluted to $10^{3.0}$ ELD50/0.4 mL. In addition, 30 one-day-old healthy ducklings were randomly divided into 3 groups. The ducklings in the test groups were inoculated with 0.4 mL of the parental strain or mutant strain by intramuscular injection, while the ducklings in the control group were inoculated with an equal volume of sterilized normal saline. The three groups of ducklings were separated and fed in different animal rooms with free access to water and feed, and observed daily after the inoculation to record the morbidity and mortality. The dead ducklings were subjected to necropsy in time, and the surviving ducklings were also subjected to necropsy after observed for 7 d to record the pathological changes in the liver, kidney and other organs of the ducklings.

No clinical symptoms were shown in the ducklings in the control group within 7 days, of which the eating and drinking behavior was normal; while the morbidity and mortality in the ducklings inoculated with the parental strain were 80% and 60%, respectively. The ducklings inoculated with the mutant strain also showed no clinical symptoms and exhibited normal eating and drinking behavior since the mutant strain underwent a significant reduction in the pathogenicity on the ducklings. Moreover, virus was detected in cloacal swabs of the ducklings inoculated with the mutant strain, which indicated that the mutant strain successfully replicated in the ducklings but was not pathogenic to the ducklings, so the mutant strain had the potential to be a candidate strain of the attenuated vaccine. The mutant strain could be distinguished from the parent strain through the combination of PCR method and DNA sequencing.

Example 3 Preparation of Inactivated Vaccine and Efficacy Evaluation

As measured in Example 2, the mutant strain CH-P60-117C had higher proliferation efficiency and virus titer in duck embryos than the parental strain, and could also proliferate in chicken embryos. Moreover, the mutant strain also had good immunogenicity and genetic stability, and significantly-reduced pathogenicity to the ducklings, and the mutant strain could proliferate in the ducklings but was not pathogenic to the ducklings. These results showed that the mutant strain ISA-A117C-T1142A-C4334A was the desired candidate strain for the preparation of DHAV-3 vaccines.

3.1 Preparation of Vaccine

As seed virus, the DHAV-3 mutant strain CH-P60-117C was diluted 100 times with sterilized normal saline, and then inoculated into the 20 9-day-old duck embryos each for 0.2 mL through the allantoic cavity. The embryos were incubated at 37° C. in the constant-temperature incubator, and then subjected to candling inspection once 24 h after the inoculation. The dead embryos were discarded, and the remaining embryos were subjected to candling inspection every 8 h, and the dead embryos were removed immediately. All the embryos were dead 48 h after the inoculation, and the collected duck embryos were placed with the air cells upright, and cooled at 4° C. for 8 h. The allantoic fluid of the duck embryos was aseptically collected and stored at −20° C. for use.

The virus solution was processed with formaldehyde solution with a final concentration of 0.1%, inactivated at 37° C. for 24 h, diluted to $10^3$ ELD50/0.1 mL with sterilized normal saline and emulsified and mixed with equal volume of Fruend's incomplete adjuvant to produce the DHAV-3 mutant strain inactivated vaccine.

3.2 Testing of Sterility and Mycoplasma

According to the appendix of the existing "Veterinary Pharmacopoeia of the People's Republic of China", the inactivated vaccine was tested for sterility and mycoplasma, and the test results were both negative.

3.3 Testing of Exogenous Virus

According to the appendix of the existing "Veterinary Pharmacopoeia of the People's Republic of China", the inactivated vaccine was tested for the exogenous virus, and the test results were all negative.

3.4 Testing of the Safety of the Vaccine

To test the safety of the vaccine, 10 one-day-old ducklings were immunized with 10 times the immunization dose, and each duckling was inoculated with 0.2 mL of the vaccine through the leg muscle. Meanwhile, 10 ducklings injected with sterilized normal saline were used as control. The ducklings were isolatedly fed with free access to water and feed. The health condition of the ducklings was observed and recorded daily, and after observed for 7 d, the ducklings were dissected. The results showed that ducklings both in the immunization group and the control group did not suffer from hepatitis, and the dissection results further showed that there were no pathological changes in the immune organs and the virus tropic tissues of the ducklings. Moreover, virus was not detected in the cloacal swab, indicating that the vaccine was not pathogenic to one-day-old ducklings.

3.5 Immune Efficacy of Vaccine 20 one-day-old ducklings were randomly divided into 2 groups, where 10 ducklings in the vaccination group were immunized respectively with one dose of the vaccine prepared above through intramuscular injection at the leg, and the other 10 ducklings were injected with equal volume of sterile normal saline and used as control. The ducklings in the two groups were isolatedly fed with free access to water and feed. After inoculation, the condition of the ducklings was observed and recorded daily. 7 d after the inoculation, the ducklings were challenged with 10 times the LD50 dose of parental strain, and then the morbidity and death of the ducklings were recorded daily. The dead ducklings were subjected to dissection and postmortem in time. After observation for 7 d, the dissection and postmortem were performed on the surviving ducklings, and the pathological changes in the liver, kidney, and other organs of the ducklings were recorded.

Within 7 days after vaccination, the ducklings in the vaccination group and the negative control group both did not show clinical symptoms, and the eating and drinking behaviors of the ducklings were normal. Two days after the virus challenge, some ducklings in the negative control group showed lassitude and neurological symptoms, and by the seventh day, a total of 6 ducklings died. The surviving ducklings suffered from different degrees of liver hemorrhage and other pathological changes. The morbidity and mortality of the control group were 80% (8/10) and 60% (6/10). The ducklings in the vaccination group did not show onset of disease or death, and had normal drinking and eating behavior, which indicated that the inactivated vaccine prepared from the mutant virus was safe and effective, protecting the ducklings from the challenge of homologous virulent viruses.

Described above are merely preferred embodiments of the application, which are merely illustrative of the concept and features of the invention and are not intended to limit the application. Any changes, replacements and modifications made without departing from the spirit of the application should fall within the scope of the application.

What is claimed is:

1. A duck hepatitis A virus-3 mutant CH-P60-117C (DHAV-3 CH-P60-117C), wherein the DHAV-3 mutant CH-P60-117C is deposited in the China Center for Type Culture Collection (CCTCC) on Dec. 2, 2018, with an accession number of CCTCC NO: V201860; wherein the DHAV-3 mutant CH-P60-117C is obtained by mutating A at position 117 of 5'-UTR of genome of a DHAV-3 virulent strain to C, mutating T at position 1142 to A to mutate tyrosine-164 of a VP0 protein of the DHAV-3 virulent strain to asparagine, and mutating C at position 4334 to A so that leucine-71 of protein 2C of the DHAV-3 virulent strain is mutated to isoleucine; wherein the DHAV-3 mutant CH-P60-117C comprises T, mutated from G, at position 3403 of the genome as a genetic marker of infectious clones; and wherein the DHAV-3 virulent strain is deposited in the China Center for Type Culture Collection with an accession number of CCTCC NO: V201305.

2. A method of constructing the DHAV-3 mutant CH-P60-117C of claim 1, comprising:

1) dividing a genome of a parental virus into a first fragment, a second fragment and a third fragment of similar size and amplifying the first fragment, the second fragment and the third fragment through PCR; adding a cytomegalovirus immediate early promoter (pCMV) (SEQ ID NO:19) to 5' end of the first fragment and introducing a first mutation site and a second mutation site respectively in 5'-UTR gene and VP0 gene of the first fragment, introducing a third mutation site in 2C gene of the second fragment and adding hepatitis delta virus ribozyme (HDVR) sequence (SEQ ID NO:20) and SV40 early mRNA polyadenylation signal (SV40 pA) sequence (SEQ ID NO:21) to 3' end of the third fragment to construct an infectious subgenomic replicon of the DHAV-3 mutant CH-P60-117C; and
2) mixing the infectious subgenomic replicon of the DHAV-3 mutant CH-P60-117C with a transfection reagent followed by transfection into duck embryo fibroblasts; wherein the infectious subgenomic replicon is transcribed in the duck embryo fibroblasts and undergoes spontaneous recombination using a homologous recombination mechanism of the duck embryo fibroblasts to form an infectious complete virus transcript, thereby leading to replication and proliferation of virus to finally obtain the DHAV-3 mutant CH-P60-117C with a genetic marker.

3. The method of claim 2, wherein in the DHAV-3 mutant CH-P60-117C, A at position 117 of 5'-UTR of genome of a DHAV-3 virulent strain is mutated to C; Tat position 1142 to A to mutate tyrosine-164 of a VP0 protein of the DHAV-3 virulent strain is mutated to asparagine; and C at position 4334 is mutated to A so that leucine-71 of protein 2C of the DHAV-3 virulent strain is mutated to isoleucine.

4. The method of claim 2, wherein there is a 74 bp overlapping region between the first fragment and the second fragment, and there is an 83 bp overlapping region between the third fragment contain and the second fragment.

5. The method of claim 2, wherein step (1) further comprises:

introducing a nonsense mutation into 2A gene of the second fragment as a site of the genetic marker.

6. A method of preparing a DHAV-3 vaccine, comprising:

inoculating the DHAV-3 mutant CH-P60-117C of claim 1 into duck embryos through allantoic cavity;

incubating the duck embryos;

collecting and cooling the duck embryos that die;

aseptically collecting an allantoic fluid from the duck embryos;

treating the allantoic fluid with a formaldehyde solution and incubating the allantoic fluid at 37° C. for 24 h to inactivate the DHAV-3 mutant CH-P60-117C;

diluting the allantoic fluid; and emulsifying the diluted allantoic fluid with an adjuvant to produce the DHAV-3 vaccine.

* * * * *